US006436693B1

(12) United States Patent
Delecluse et al.

(10) Patent No.: US 6,436,693 B1
(45) Date of Patent: Aug. 20, 2002

(54) METHOD FOR HELPER VIRUS-FREE PACKAGING OF A GENE VECTOR DNA

(75) Inventors: Henri-Jacques Delecluse; Dagmar Pich; Wolfgang Hammerschmidt, all of Munich (DE)

(73) Assignee: GSF Forschungszentrum fur Umwelt und Gesundheit GmbH, Oberschlesibheim (DE)

(*) Notice: Subject to any disclaimer, the term of this patent is extended or adjusted under 35 U.S.C. 154(b) by 0 days.

(21) Appl. No.: 09/184,986

(22) Filed: Nov. 3, 1998

(30) Foreign Application Priority Data

Nov. 5, 1997 (DE) .......................... 197 48 895
Mar. 27, 1998 (DE) .......................... 198 13 775

(51) Int. Cl.[7] .............. C12N 7/01; C12N 7/02; C12N 5/10; C12N 15/869

(52) U.S. Cl. ............... 435/235.1; 435/239; 435/320.1; 435/325; 435/366

(58) Field of Search ............. 435/235.1, 239, 435/320.1, 325, 366, 455, 456, 457, 472, 475, 254.11

(56) References Cited

U.S. PATENT DOCUMENTS

| | | | |
|---|---|---|---|
| 5,194,601 A | | 3/1993 | Sugden et al. |
| 5,354,678 A | * | 10/1994 | Lebkowski et al. ...... 435/235.1 |
| 5,716,845 A | | 2/1998 | Sugden et al. |

FOREIGN PATENT DOCUMENTS

| | | |
|---|---|---|
| EP | 694613 | 6/1995 |
| WO | 9629421 | 9/1996 |
| WO | 9705263 | 2/1997 |

OTHER PUBLICATIONS

Messerle et al (PNAS 94:14759–63, Dec. 1997).*
Roizman et al. "Herpes Simplex Viruses and Their Replication." Fields Virology, Third Edition, ed. B.N. Fields et al, Lippencott–Raven Publishers, Philadelphia, p. 849–895, 1996.*
Moss et al. "Replication of Poxviruses." Virology, ed. B.N. Fields et al, Raven Press, New York, p685–703, 1986.*
Kieff. "Epstein–Barr Virus and Its Replication". Fields Virology, Third Edition, ed. B.N. Fields et al, Lippencott–Raven Publishers, Philadelphia, p. 2343–2396, 1996.*
Stavropoulos et al (Journal of Virology 72(9):7137–7143, Sep. 1998).*
Suter, et al, "BAC–VAC, a novel generation of (DNA) vaccines: A bacterial artificial chromosome (BAC) containing a replication–competent, packaging–defective virus genome induces protective immunity against herpes simplex virus 1", PNAS, Oct. 26, 1999, vol. 96, No. 22, 12697–12702.

Xiao et al, "Production of High–Titer Recombinant Adeno–Associated Virus Vectors in the Absence of Helper Adenovirus", Journal of Virology, Mar., 1998, pp. 2224–2232.
Naldini, et al., "In Vivo Gene Delivery and Stable Transduction of Nondividing Cells by Lentiviral Vector" Apr. 12, 1996, pp. 263–267.
O'Connor, et al. "Construction of Large DNA Segments in *Escherichia coli*" Jun. 16, 1989, pp. 1307–1312.
Kempkes et al., "Immortalization of human primary B lymphocytes in vitro with DNA" Jun. 1995, pp. 5875–5879.
Kempkes et al., "Immortalization of Human B Lymphocytes by a Plasmid Containing 71 Kilobase Pairs of Epstein–Barr Virus DNA" Jan. 1995, pp. 231–238.
Leib et al., "Gene Delivery to Neurons: Is Herpes Simplex Virus the Right Tool for the Job?" Aug. 1993, pp. 547–554.
Baer et al., "DNA Sequence and Expression of the B95–8 Epstein–Barr virus Genome" Jul. 1984, pp. 207–211.
Cohen, et al., "Epstein–Barr virus nuclear protein 2 is a key determinant of lymphocyte transformation" Dec. 1989, pp. 9558–9562.
Hammerschmidt et al., "Identification and Characterization of OriLyt, a Lytic Origin of DNA Replication of Epstein–Barr Virus" Nov. 4, 1988, pp. 427–433.
Hammerschmidt et al., "Genetic analysis of immortalizing functions of Epstein–Barr virus in human B lymphocytes" Aug. 1989, pp. 393–397.
Kempkes, et al., "Immortalization of human primary B lymphocytes in vitro with DNA" Jun. 1995, pp. 5875–5879.
Kempkes et al., "Immortalization of Human B Lymphocytes by a Plasmid Containing 71 Kilobase Pairs of Epstein–Barr Virus DNA" Jan. 1995, pp. 231–238.
Moore et al., "Molecular cloning of the CDNA encoding the Epstein–Barr virus/C3d receptor (complement receptor type 2) of human B lymphocytes" Dec. 1987, pp. 9194–9198.
Nemerow et al., "Identification of an Epitope in the Major Envelope Protein of Epstein–Barr Virus that Mediates Viral Binding to the B Lymphocyte EBV Receptor (CR2)", Feb. 1989, pp. 369–377.
Yates et al., "Stable Replication of plasmids derived from Epstein–Barr virus in various mammalian cells" Feb. 1985, pp. 812–815.
Zimmerman et al., "Structure and Role of the Terminal Repeats of Epstein–Barr Virus in Processing and Packaging of Virion DNA", May 1995, pp. 3147–3155.
Cherepanov et al., "Gene disruption in *Escherichia coli*: Tc$^R$ and Km$^R$ cassettes with the option of Flp–catalyzed excision of the antibiotic–resistance determinant".

(List continued on next page.)

*Primary Examiner*—Mary E. Mosher
(74) *Attorney, Agent, or Firm*—Nixon & Vanderhye P.C.

(57) ABSTRACT

The present invention relates to a method for helper virus-free packaging of gene vector DNA into the virus particles of a DNA virus as well as to eukaryotic helper cells for helper virus-free packaging of gene vector DNA into the virus particles of a DNA helper virus wherein a DNA virus having a genome $\geq 100$ kbp is employed (FIG. 1).

15 Claims, 9 Drawing Sheets

OTHER PUBLICATIONS

Hanahan "Studies on Transformation of *Escherichia coli* with Plasmids" 1983, pp. 557–580.

Firth, et al. "Structure and Function of the F Factor and Mechanism of Conjugation" pp. 2377–2401.

Shizuyza, et al. "Cloning and stable maintenance of 300–kilobase–pair fragments of human DNA in *Escherichia coli* using an F–factor–based vector" Sep. 1992, pp. 8794–8797.

* cited by examiner

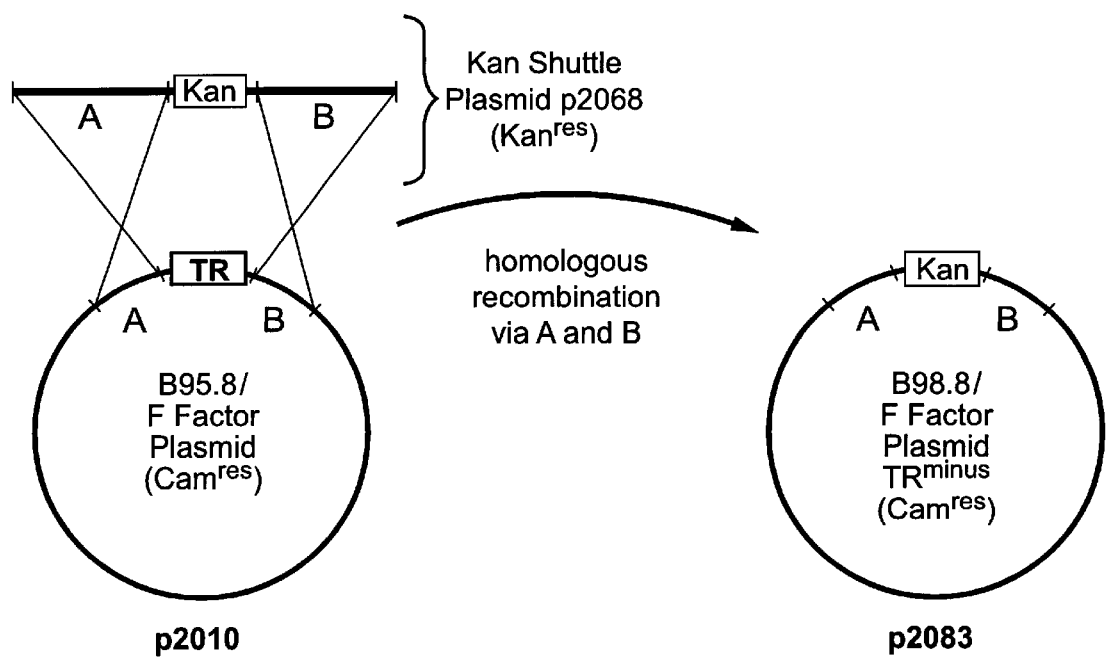
Figure 1: Deletion of the packaging signal sequences TR in the B95.8/F factor plasmid p2010 and exchange against a selectable marker in E.coli

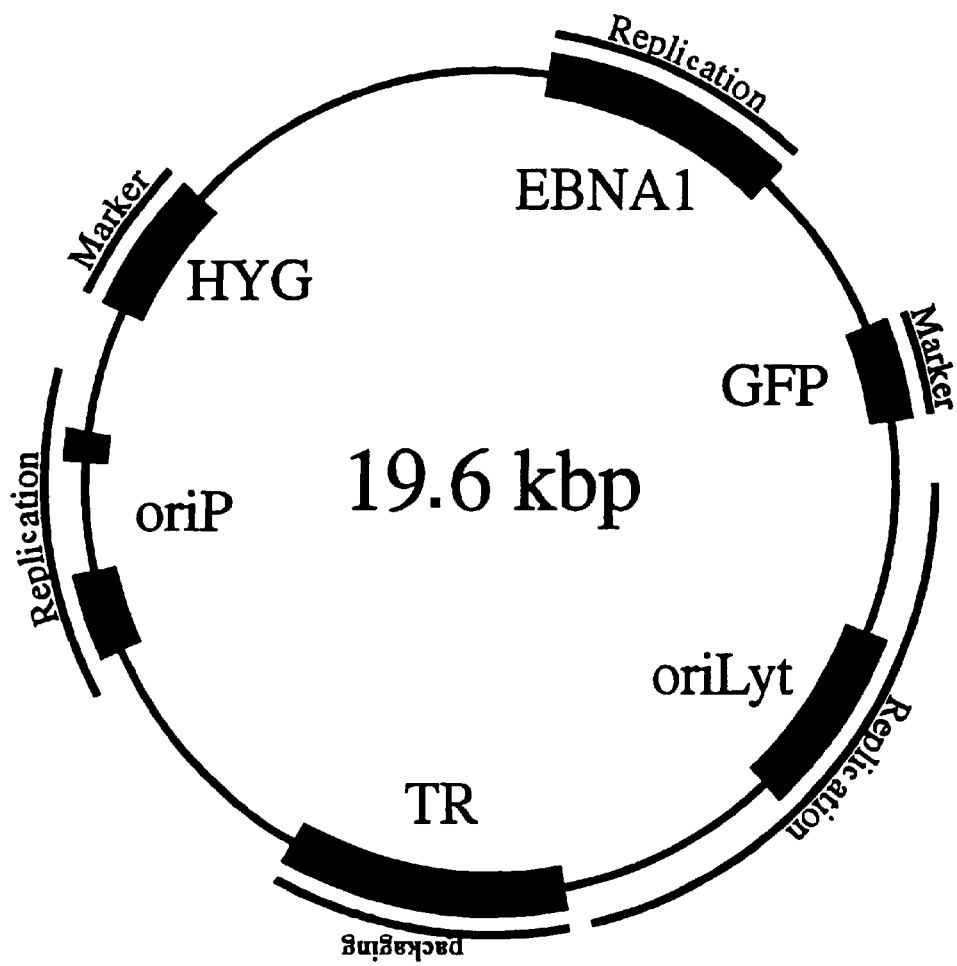
Figure 2: Map of the p2186.31 gene vector showing the cis-acting herpes virus elements oriP, oriLyt, TR, the selectable marker hygromycin phosphotransferase HYG, the gene for 'green fluorescence protein' GFP, and the viral gene EBNA1 for extrachromosomal replication of the gene vector in eukaryotic cells

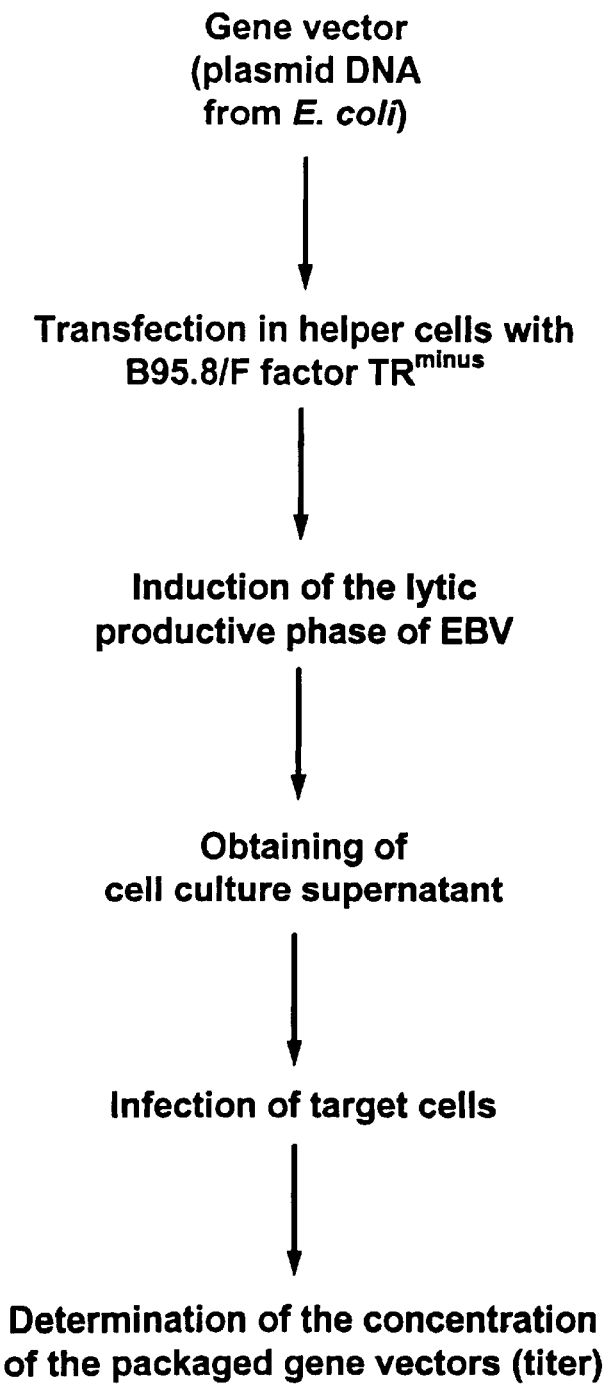
Figure 3: Packaging of herpes viral gene vectors using helper virus-free packaging cell lines (helper cells).

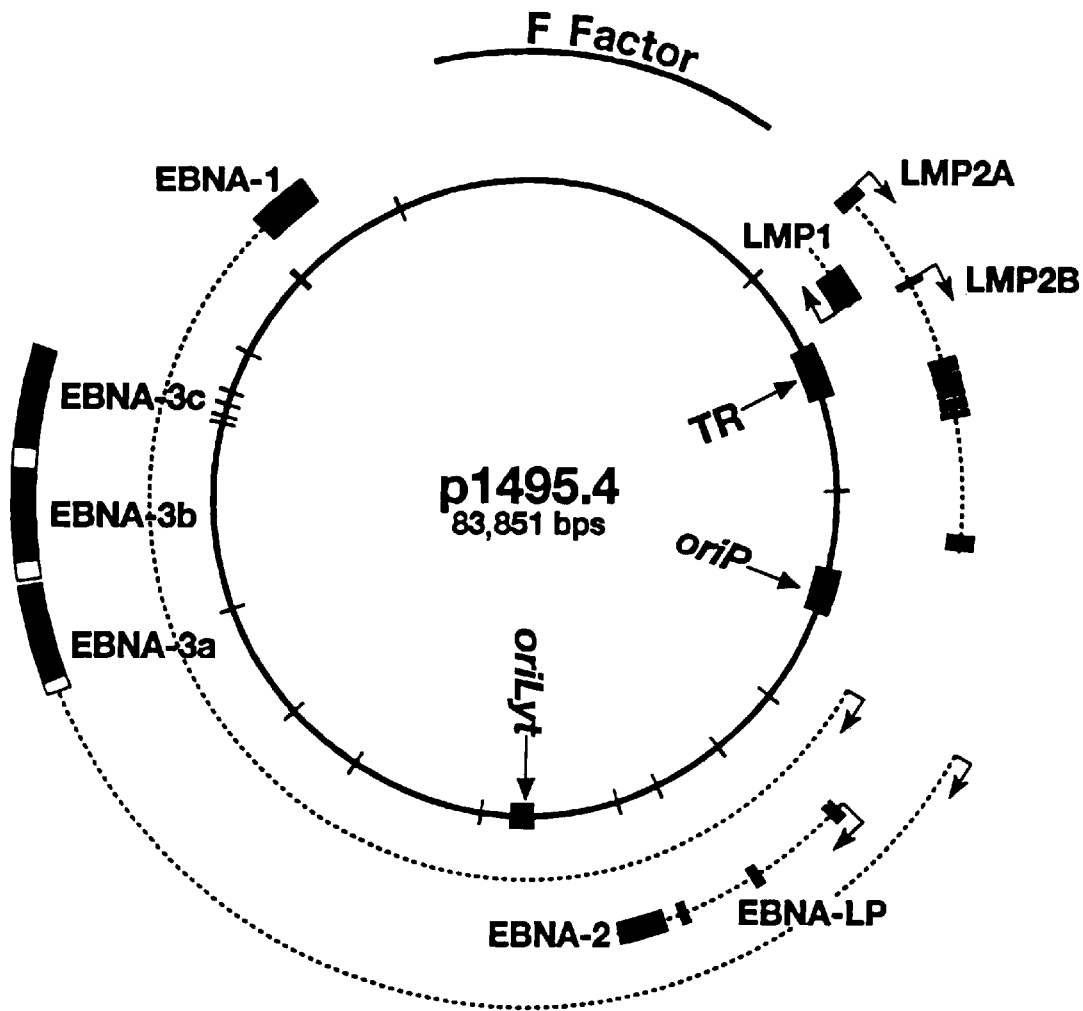
Figure 4: Gene map of EBV mini plasmid p1495.4 as a herpes virus gene vector showing the cis-acting elements oriP, oriLyt, TR. The viral genes LMP and EBNA shown are involved in B cell immortalization

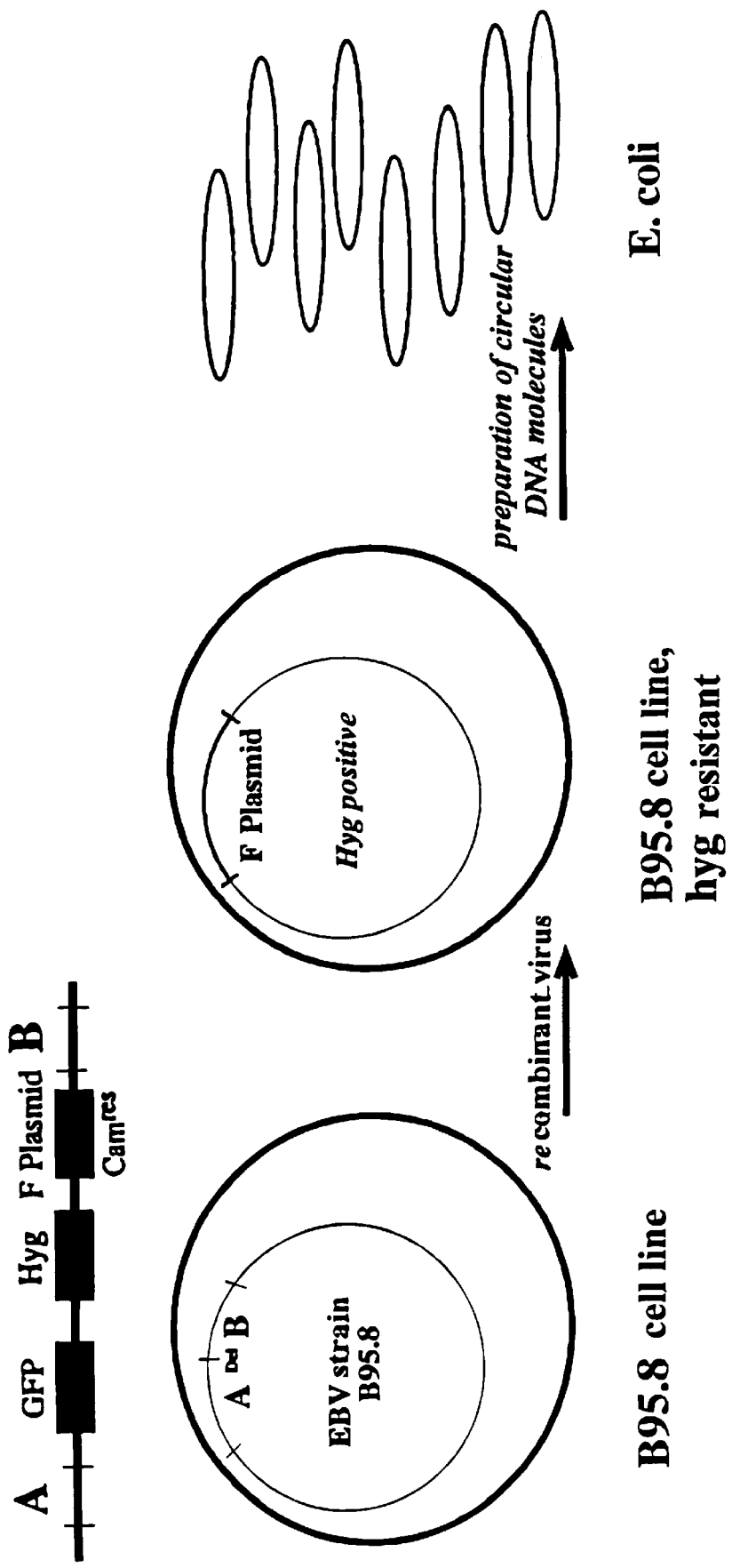
Figure 5: Cloning of genomic B95.8 DNA in E. coli using a F factor plasmid

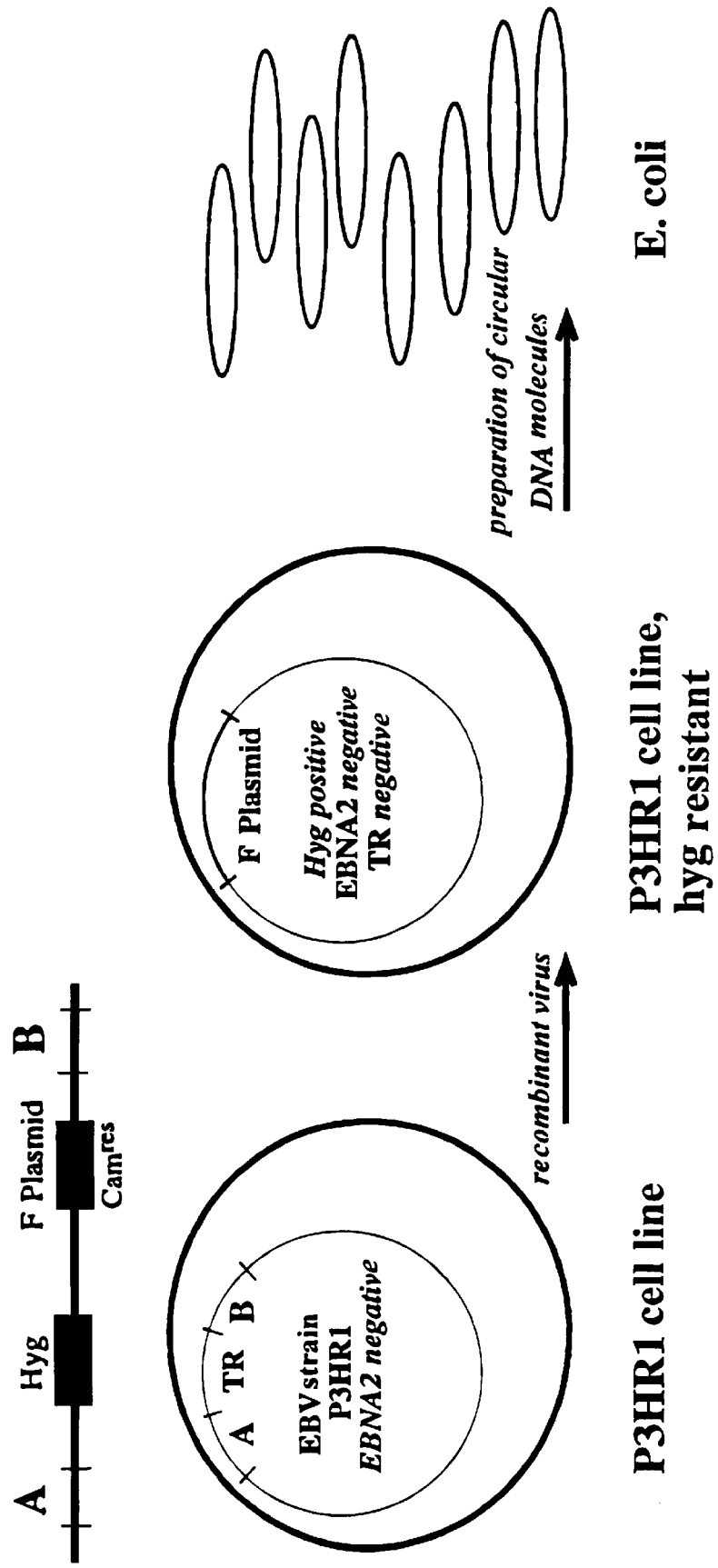
Figure 6: Cloning of genomic P3HR1 DNA without packaging signals (TR) in E. coli using an F factor plasmid

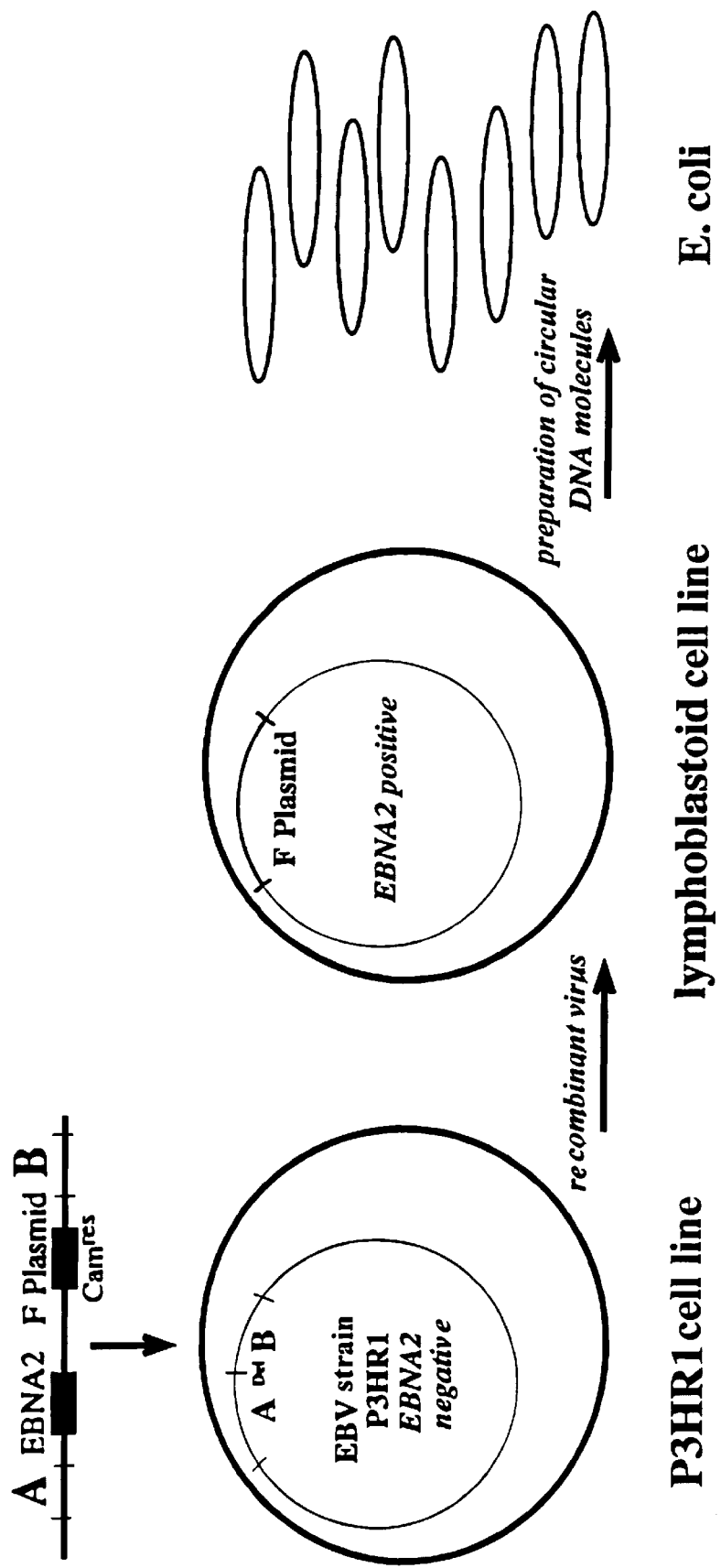

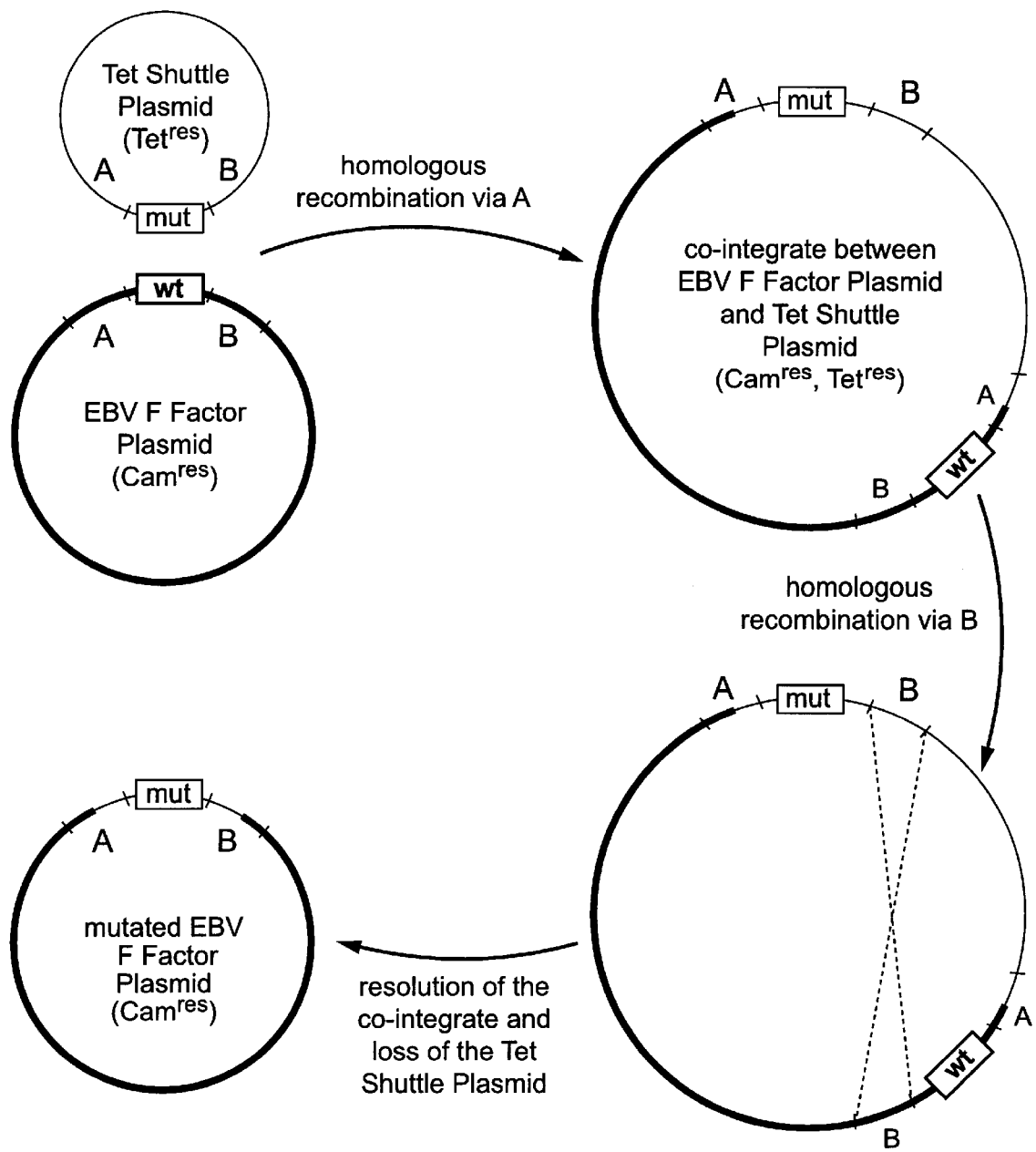
Figure 8: Introduction of mutations in genomic EBV DNA cloned into F factor by allelic exchange

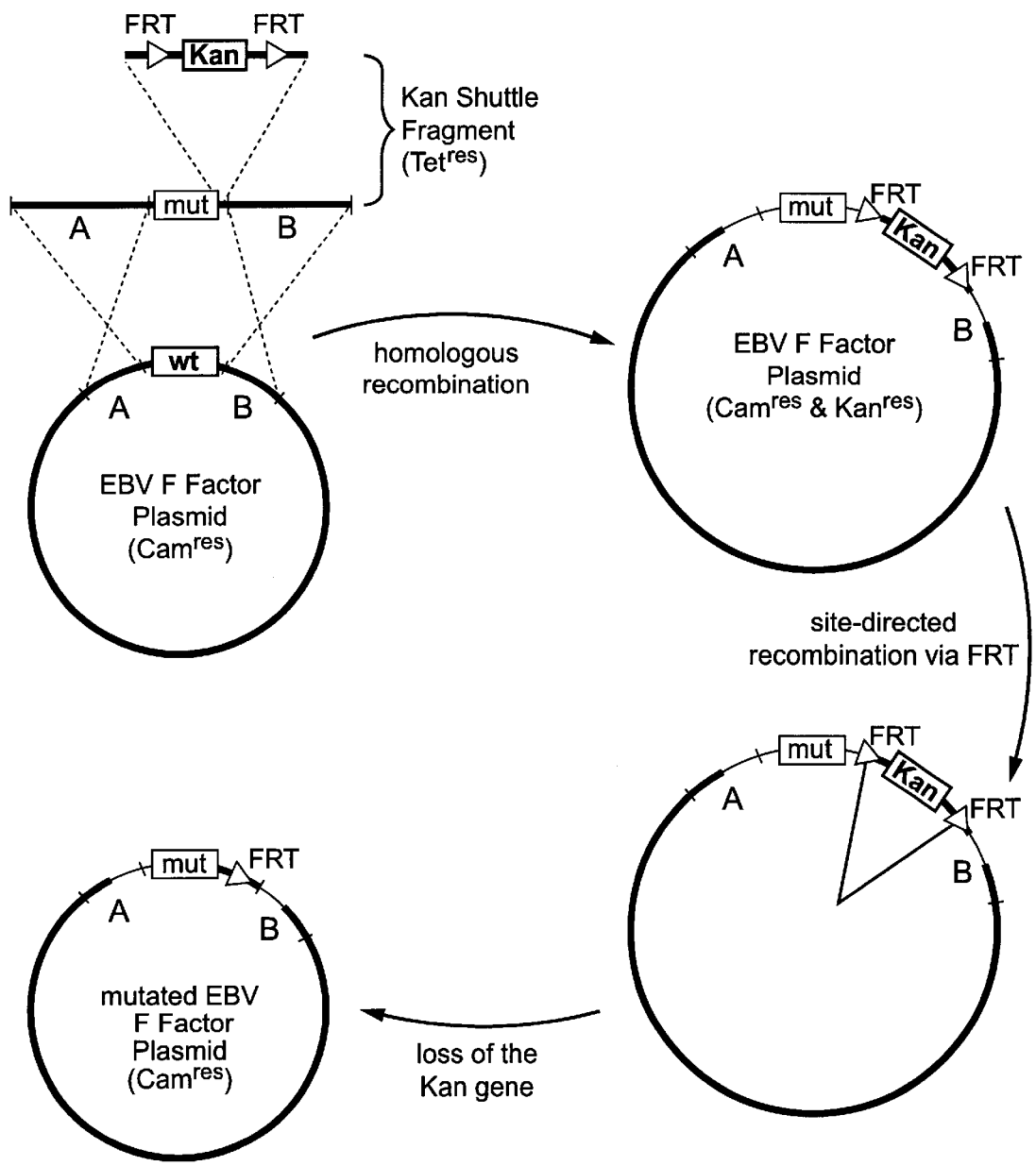
Figure 9: Introduction of mutations into genomic EBV DNA cloned into F factor by selective integration

METHOD FOR HELPER VIRUS-FREE PACKAGING OF A GENE VECTOR DNA

BACKGROUND OF THE INVENTION (i) Field of the Invention

The present invention relates to a method for helper virus-free packaging of gene vector DNA into the viral particles of a DNA virus as well as to eukaryotic helper cells for helper virus-free packaging of gene vector DNA into the viral particles of a DNA helper virus wherein a DNA virus having a genome $\geq 100$ kbp is used.

(ii) Description of the Related Art

Epstein-Barr-virus (EBV) is one of eight known herpes viruses in humans. The DNA sequence of the EBV B95.8 isolate has been determined (Baer et al., 1984), and detailed scientific evidence has been worked out mainly with respect to DNA elements which play important roles in the two EBV phases. In the so-called 'latent phase' the virus establishes a stable host cell relation during which the vitality of the cell remains unaffected, however, the viral DNA genome is replicated in the form of an extrachromosomal plasmid in the host cells and passed on into the daughter cells. The latent phase may be associated with a transformation or immortalization, respectively, of the cells infected in latent manner. The replication origin of the plasmid, oriP, is the DNA element essential for maintenance and replication of the EBV genome in the latent phase. (Yates et al., 1985). This DNA element is also active in recombinant plasmids and has been used as such in several ways.

In the so-called 'lytic or productive phase' the virus is released which involves the expression of almost all of the viral proteins necessary for gene regulation or production of structural viral components, respectively. The lytic phase also requires two other DNA elements of the virus: the lytic origin of replication, oriLyt, is responsible for viral DNA amplification (Hammerschmidt and Sugden, 1988), the terminal repeats, TR, which represent packaging signals indispensable for encapsidation of the amplified EBV DNA (Hammerschmidt and Sugden, 1989; Zimmermann and Hammerschmidt, 1995).

There is a broad interest in the genetic analysis of EBV functions, construction of recombinant EBV genomes, as well as in EBV gene vectors. There is particular interest in the gene vectors because additional therapeutically relevant genes may be introduced into suitable recipient cells. In this respect, however, the co-transfer of undesired EBV genes into the target cells must be excluded. This problem has to be solved to comply with the requirements for saftey of this novel form of therapy and to be able to use herpes virus gene vectors in gene therapy in humans.

The strategy in the production of gene vectors is directed to provide only the gene vectors themselves with a viral capsid while the release of so-called helper viruses is prevented. This is achieved by removing or mutating cis-acting DNA elements of the helper virus genome necessary for the production of the helper virus itself. To date it was impossible to genetically manipulate the portions of the EBV genome which are indispensable for the maturation of viral particles. Thus, it was impossible to switch-off functions of EBV or other herpes viruses which are for example absolutely required for the packaging of the viral genome. Up to now, cell lines have been conventionally used which were infected by herpes viruses in a targeted manner to utilize all of the viral functions for gene vector amplification. The simultaneous amplification of the infectious virus and the packaging of its genome into a viral capsid was unavoidable. Similarly up to now also we used cell lines which were infected by EBV in a latent manner. In this case also the lytic functions of the virus are necessary for packaging of suitable gene vectors so that an amplification of the helper virus genome and subsequent packaging was unavoidable (Hammerschmidt and Sugden, 1989; Kempkes et al., 1995b).

DISADVANTAGES OF THE RELATED ART

Viral gene vectors are an important instrument in gene therapy. However, it must be ensured that in their preparation and therapeutical use viral gene vectors are prepared which do not contain any virus. Since certain viral gene functions are indispensable for the production of viral gene vectors it is impossible to avoid the use of so-called helper viruses or the functional segments thereof. This particularly applies to complex viral systems relying on numerous virus-encoded functions. Thus, EBV for example encodes more than 80 genes, of which about 50 are indispensable for viral synthesis. Since these genes in their entirety are present on the viral genome in a single DNA molecule certain properties have to be missing from the genome to prevent its packaging into virus particles and its release together with the gene vector. One possiblity to prevent this release of the helper virus is to delete the cis-acting portions of the genome which are essential for the packaging of the helper virus genome itself. In EBV, these genomic regions are referred to as TR (TR=terminal repeats) sequences, in other herpes viruses as pac sequences (pac=packaging). Alternatively, also other regions may be deleted or their function may be abolished which are indispensable for helper virus genome replication in cis. In EBV, this would be the lytic origin of replication, oriLyt, the functional equivalent of which is named oriS or oriL in other herpes viruses.

The deletion of these regions prevents helper virus release; however it also prevents the possibility to generate or even to introduce the helper virus itself via infection into the cells considered for packaging of the viral gene vector. Since these properties mutually exclude each other it has been impossible to date to establish cell lines capable of producing herpes virus gene vectors without releasing helper viruses. The same is true for gene vectors derived from other viral systems which have viral genomes of a size of more than 100 kb. In addition, it is also impossible to avoid this disadvantage by biochemical separation of helper virus and gene vector because both particles differ only with respect to their genetic but not their external or physical composition. Our invention permits for the first time to overcome said disadvantage.

SUMMARY AND OBJECTS OF THE INVENTION

It is an object of the present invention to provide a method of packaging of a gene vector DNA into the virus particles of a DNA virus using on the one hand the proteins for the production of viral particles of a DNA virus having a genome $\geq 100$ kbp and on the other hand avoiding the packaging of helper virus DNA into the viral particles. This object has been solved by the method having the following steps of:

a) Introduction of a DNA helper virus vector DNA on one or more molecules having at least the following features:
  (α) a total size of $\geq 100$ kbp;
  (β) having at least one mutation designed to render one or more of the cis-acting signal sequences for packaging of the DNA helper virus vector DNA non-functional;

(γ) having the information for the production of DNA virus particles of the DNA helper virus which do not contain a helper virus genome; into an eukaryotic cell;

(b) introduction of a gene vector DNA to be packaged having at least
   (α) a cis-acting signal sequence for packaging of the gene vector DNA into a viral particle of the DNA helper virus;
   (β) a gene of interest; into the eukaryotic cell;

(c) induction of the lytic phase of the DNA helper virus and production of the proteins important for packaging of the DNA helper virus;

(d) packaging of the gene vector DNA into the viral particles of the DNA helper virus; optionally (e) releasing the viral particles containing the gene vector DNA; and/or optionally (f) purifying the viral particles.

According to the invention the DNA helper virus vector DNA may be present not only on one molecule but for example also on two or more molecules, the total size of the molecules being ≧100 kbp.

The DNA helper virus vector DNA is mutated so that one or more of the cis-acting signal sequences for packaging of the DNA are non-functional, i.e. the helper virus DNA may provide the informations necessary for production of the viral particles but may not be packaged into viral particles itself.

The gene vector DNA to be packaged contains such cis-acting signal sequences necessary for its packaging into a virus particle of the DNA helper virus. Furthermore, the DNA to be packaged contains a gene of interest. In further embodiments of the invention at least one marker gene selectable in prokaryotes and/or eukaryotes may be additionally present.

Following induction of the lytic phase of the DNA helper virus the proteins of the DNA helper virus essential for packaging are produced while in a subsequent step the gene vector DNA is packaged into the viral particles of the DNA helper virus formed. Since the DNA helper virus vector DNA lacks signal sequences for packaging the helper virus DNA is not packaged into the viral particles.

The eukaryotic helper cell containing the DNA helper virus viral particles with the packaged gene vector DNA may be used in the present form where, however, also the virus particles may be released and may optionally be purified, isolated and/or concentrated.

In a preferred embodiment of the invention the DNA helper virus vector DNA contains at least portions of the EBV DNA. In the case of EBV being the DNA helper virus there may be mutated as the cis-acting signal sequence in the helper virus DNA the terminal repeat sequences of EBV, the lytic origin of replication of EBV, the plasmid origin of replication oriP of EBV, or the EBNA1 gene of EBV so that they are no longer capable of exerting their function as cis-acting signal sequence for packaging. On the other hand, these signal sequences may be employed in the gene vector DNA to be packaged as packaging signals in functional form.

Marker genes which may be selected for in prokaryotic cells and/or eukaryotic cells are known per se. Examples are antibiotic resistance genes or genes encoding a protein detectable by fluorescence.

The eukaryotic cell employed may be any cell compatible with the DNA helper virus vector DNA.

In a preferred embodiment of the invention a gene is introduced into the eukaryotic cell for affecting the cell tropism of the DNA helper virus wherein this gene is located either on a plasmid different from the gene vector DNA or is arranged on the gene vector DNA. This gene encodes a protein integrated into the viral particle so that the cell tropism thereof is altered. It should be understood, if desired or necessary, that it is also possible to use several genes encoding several proteins to alter the cell tropism.

In a further embodiment of the invention eukaryotic helper cells are provided for helper virus-free packaging of gene vector DNA into the viral particles of a DNA helper virus wherein the helper cell at least contains:

(a) a DNA helper virus vector DNA ≧100 kbp on one or more molecule(s) carrying a mutation designed to render one or more of the cis-acting signal sequences for packaging non-functional and having the information for the production of DNA virus particles lacking a helper virus genome;

(b) a gene vector DNA having at least
   (α) a cis-acting signal sequence for packaging of the gene vector DNA into DNA helper virus viral particles;
   (β) a gene of interest.

In another embodiment of the invention the gene vector DNA further contains one or more marker genes selectable in prokaryotes and/or eukaryotes.

It should be understood that the eukaryotic helper cell may contain further DNA segments for example in the form of plasmids. The DNA helper virus vector DNA and the gene vector DNA present in the eukaryotic helper cell may be developed as described above.

The eukaryotic helper cell of the present invention may for example contain as the DNA helper virus vector DNA a herpes virus DNA preferably an EBV DNA or at least portions thereof. It is for example a human cell, however, as already detailed above any cell may be used which is compatible with the helper virus.

According to the invention preferably a herpes virus, particularly the EBV, is used as the DNA helper virus. The helper virus-free packaging of a gene vector DNA into the capsid of a DNA virus having a genome ≧100 kbp is possible for the first time and was enabled by establishing a technology permitting the cloning of the entire genome of DNA viruses ≧100 kbp into prokaryotes and the modification of any segment of this large DNA genomes in prokaryotes but also in eukaryotes. Thus, it has been possible for the first time to genetically alter also those segments of DNA viruses ≧100 kbp which are absolutely essential for the viral functions in eukaryotic cells. Examples for such functions in EBV are both the origins of DNA replication of EBV, oriLyt and oriP, and the packaging signals of the viral DNA, the so-called terminal repeats.

By this technique it was possible to switch off the functions for packaging and/or DNA replication of the helper virus genome in a targeted manner. Starting point is the cloning of the genome of DNA viruses ≧100 kbp, such as that of EBV, into a prokaryotic cell, such as in *E. coli,* in the form of a recombinant plasmid. This was the milestone required for modification of all of the segments of DNA viruses ≧100 kbp via conventional recombinant DNA technologies in prokaryotes. This modification also involves those genomic segments of DNA viruses which are essential for the replication of the viral genome and its packaging in eukaryotic cells. The deletion or loss of function of these genomic segments in the prokaryotic cell has no consequences in the prokaryotic cell since for example the EBV segments represent only the—very large—insert in an *E. coli* replicon which have no importance for replication and maintenance of the replicon in *E. coli*. The viral genome thus modified in a prokaryotic cell may be isolated in the form of plasmid DNA which may then be introduced into suitable eukaryotic cells via conventional DNA transfection techniques. This method of preparation permits the establishment of helper virus genomes able to package viral gene vectors into a viral capsid but which themselves may no longer be released. In the following this method is described in more detail. The description is particularly based on the cloning of the entire EBV genome as a plasmid into an *E. coli* cell. However, the cloning of EBV and the preparation of a packaging-free helper cell line providing the EBV capsid should only be understood as an exemplary embodiment of the invention. Generally, the invention may also be applied to other DNA viruses having a genome $\geq 100$ kbp, for example other herpes viruses, but also to pox viruses, baculoviruses or iridio viruses.

DESCRIPTION OF THE DRAWINGS

FIG. 1: Schematic illustration depicting deletion of the packaging signal sequences TR in the B95.8/F factor plasmid p2010 and exchange against a selectable marker in *E. coli*;

FIG. 2: A map of the p2186.31 gene vector;

FIG. 3: A flow chart illustrating the packaging of herpes viral gene vectors using helper virus-free packaging cell lines (helper cells);

FIG. 4: A gene map of EBV mini plasmid p1495.4 as a herpes virus gene vector;

FIG. 5: The cloning of genomic B95.8 DNA in *E. coli* using a F factor plasmid;

FIG. 6: The cloning of genomic P3HR1 DNA lacking packaging signals (TR) in *E. coli* using a F factor plasmid;

FIG. 7: the cloning of genomic P3HR1 DNA in *E. coli* using a F factor plasmid;

FIG. 8: The introduction of mutations into the EBV DNA cloned into F factor by allelic exchange; and FIG. 9: The introduction of mutations into the EBV DNA cloned into F factor by selective integration.

DETAILED DESCRIPTION OF PREFERRED EMBODIMENTS

In the following, the invention will be described in more detail with respect to Examples and to Figures. The invention will be explained with respect to an EBV helper virus vector DNA. However, it should be understood that this represents only an exemplary embodiment of the invention. According to the invention, also other helper viruses, another gene vector DNA etc. may be used. The invention is not limited to the following Examples.

As the starting material for the preparation of a helper virus genome suitable for a packaging cell line for herpes virus gene vectors served plasmids from *E. coli* carrying the entire EBV genome of the B95.8 EBV strain. The preparation of such EBV/F factor plasmids is described in the following. To remove the cis-acting segments important for packaging of the virus the terminal repeats were deleted from the EBV/F factor plasmid in *E. coli* or the prokaryotic selection marker kanamycin phosphotransferase was inserted into this site, respectively. The individual steps of this method are presented in FIG. 1. Alternatively, the deletion of this cis-acting element may also be achieved using other methods. The problem may also be solved by rendering the so-called lytic origins of replication of EBV non-functional so that no replicative intermediate of the viral genome is produced which is a prerequisite for its packaging.

The recombinant EBV/F factor plasmid thus altered may be isolated from *E. coli*, and the DNA molecules may be prepared using conventional methods. These DNA molecules are then transferred stably or transiently into eukaryotic cells using DNA transfer techniques. The recombinant EBV genomes undergo extrachromosomal replication in these cells similar to cell lines infected by EBV in a latent manner. In these cell lines the lytic phase of EBV may be induced leading to the expression of all proteins important for virus synthesis. Basically in these cells these proteins are also available in trans for DNA replication and packaging of other recombinant plasmids, so-called mini EBV plasmids or gene vectors, into viral particles (Hammerschmidt and Sugden, 1988; Hammerschmidt and Sugden, 1989).

Since the modified EBV/F factor plasmid lacks the cis-acting DNA elements essential for its packaging, the synthesis of empty defective Epstein-Barr virus particles occurs which carry no genetic information but may be released into the cell culture supernatant. Thus, a cell line has been generated providing all functions necessary for packaging of viral gene vectors except that the packaging of the EBV/F factor plasmid as a helper virus genome is impossible. Such cell lines are also referred to as helper virus-free packaging cell lines.

Viral gene vectors are recombinant plasmids generally produced by conventional molecular biological cloning methods. For most of the gene vectors at least two viral genomic regions are necessary which are required in cis on the recombinant plasmid. These two regions are the packaging signals essential for encapsidation of the gene vector DNA into viral particles. On the other hand the origin of replication must be present on the DNA molecule. Amplification of the gene vector DNA effected by the origin of replication is not only necessary for DNA replication and increase in copy number of the gene vector DNA but mainly for the synthesis of replicative DNA intermediates. In the case of herpes viruses these DNA intermediates are concatemeric DNA molecules consisting of many copies of the starting DNA molecules arranged in a tandem-like manner. It is generally accepted that these replicative DNA intermediates are required for encapsidation of nucleic acid molecules into viral particles. However, also the packaging signals are important for the encapsidation step, as already described above.

Viral gene vector plasmids which in the case of EBV carry the packaging signals TR and the lytic origin of replication oriLyt besides the prokaryotic portions of the plasmid necessary for propagation in *E. coli* are basically suitable for packaging into an EB viral capsid. Such gene vector plasmids are introduced into the helper virus-free packaging cell line in transient or stable form, and the lytic phase of EBV is induced. The viral proteins provided by the EBV/F factor plasmid as the helper virus genome lead to DNA replication of the viral gene vector plasmid, packaging of the gene vector DNA into viral particles and their release.

EXAMPLES

1. Deletion of TR regions on an EBV/F Factor Plasmid as a Helper Virus Genome

An EBV/F factor plasmid named p2010 was modified in *E. coli* using known methods so that the TR packaging signals have been deleted and the prokaryotic marker gene kanamycin phosphotransferase has been introduced at this site. As shown schematically in FIG. 1 this alteration in the EBV/F factor plasmid was generated by the technique referred to as selective integration. Details of the proceeding have been included in FIG. 1 or are described in the text accompanying the Figure, respectively. The modified EBV/F factor plasmid has been named p2083.

Alternative methods for genetic modification of genomic EBV DNA cloned into F factor are available and are described in the following. Any antibiotic resistance marker and sequences employed for recombination may be used.

The TR minus EBV/F factor plasmid p2083 was isolated from E. coli and transferred into the human 293 cell line using conventional DNA transfection techniques. The TR minus EBV/F factor plasmid bears the gene for the eukaryotic selection marker hygromycin phosphotransferase. The transfected 293 cells were selected with appropriate hygromycin concentrations. Single cell clones were subjected to functional analysis of their properties.

2. Characterization of the Helper Virus-free Packaging Cell Line

A viral gene vector p2186.31 was constructed as a plasmid using conventional DNA cloning techniques as shown in FIG. 2. This plasmid serves as a reporter plasmid for the characterization of the packaging functions of 293 cells carrying the TR minus EBV/F factor plasmid. Besides the TR packaging sequences and the lytic origin of replication, oriLyt, the viral gene vector also bears other viral sequences essential for extrachromosomal replication of the gene vector in the recipient cell. Those sequences are the origin of replication of the plasmid, oriP, and the EBNA1 gene (FIG. 2). Moreover, the gene vector harbours the gene for the 'green fluorescence protein' and the gene for resistance against hygromycin. The viral gene vector is introduced into these cells in transient manner, as shown in FIG. 3, and at the same time the lytic cycle of EBV is induced using an expression plasmid for the BZLF1 viral gene, as described (Hammerschmidt and Sugden, 1989). The supernatant of these cells contains a gene vector packaged into an EBV capsid. Analysis and determination of the concentration of this gene vector is carried out by infection of suitable cells having the EBV receptor, e.g. Raji cells. Successful infection of Raji cells with the gene vector p2186.31 may simply be determined by the fluorescence of the 'green fluorescence protein' because cells infected with the gene vector appear green when observed in the light microscope under UV light.

Moreover the successful transfer of the gene vector DNA p2186.31 may be determined by selection of the infected Raji cells by hygromycin. The subsequent DNA analysis of the hygromycin-resistant Raji cells using the Southern blot technique and appropriate radiolabeled DNA probes confirms the presence of intact gene vector DNA and the absence of TR minus EBV/F factor plasmid or portions thereof.

Alternatively, there may be used a plasmid as the viral gene vector lacking the oriP and EBNA1 segments or carrying one or more genes of therapeutical interest instead of the gene for the 'green fluorescence protein' GFP. In addition, the hygromycin phosphotransferase selection marker may be optionally omitted or be replaced by another gene.

Alternatively, a mini EBV plasmid may be used as the viral gene vector containing besides the viral sequences for oriLyt, TR, EBNA1, and oriP also other genes necessary for immortalization of human B cells. The properties of such mini EBV plasmids have been described by us, and an example is shown in FIG. 4 (Hammerschmidt and Sugden, 1989; Kempkes et al., 1995a; Kempkes et al., 1995b). This mini EBV plasmid may also be introduced into the packaging cell lines in transient or stable form, the EBV lytic cycle may be induced, and the cell supernatant examined for packaged mini EBV plasmids. The supernatant is used to infect human primary B lymphocytes which then grow as immortalized permanently proliferating B cell lines. All B cell lines contain one or more copies of the mini EBV plasmid but lack TR minus EBV/F factor plasmids or portions thereof.

3. Gene Vectors for Transduction into Specific Cells

Gene vectors transfer genes in such cells which are normally infected by the corresponding helper viruses. By helper cell lines it is possible to affect the so-called cell tropism. Glycoproteins of herpes viruses responsible for the infection of certain cells (naturally B cells and some epithelial cells in the case of EBV) may be altered or replaced by others by means of mutating the EBV genomes cloned into F factor in E. coli. An example for an extended cell tropism is the vesicular stomatits virus glycoprotein G, an example for an extremely specific cell tropism for almost exclusively pluripotent hematopoietic stem cells is the ligand of stem cell factor receptor on the stem cell, the membrane-bound stem cell factor ligand (mSCF ligand). This process is referred to as pseudo-typing and is particularly attractive for herpes virus vectors. In herpes viruses, the glycoproteins important for infectiousness are embedded in a phospholipid membrane derived from a nuclear membrane. This membrane is essentially unstructured and only loosely encapsulates the strictly geometrical capsid of the virion. In contrast to capsidless viruses (e.g. adenoviruses, adeno-associated virus (AAV)) or other encapsidated viruses (e.g. retroviruses) the capsid of herpes viruses and other large DNA viruses is flexible and requires no specific structure, protein configuration or folding which otherwise would prevent virus maturation and assembly. This is the prerequisite for providing the gene vectors with other glycoproteins and thus with novel properties with respect to their cell tropism.

In the case of EBV two glycoproteins are considered to be important in the infection of cells. The gp350/220 glycoprotein-is important for the adsorption of the viral particles to the cellular receptor (Moore et al., 1987; Nemerow et al., 1989). This receptor has also been named CD21. The viral glycoprotein gp85 is involved in the fusion of the herpes virus capsid with the cellular plasma membrane. The counter-receptor on the cell seems to be a MHC class II molecule. For cell targeting mainly gp350/220 is important.

We have used two methods for the alteration of the cell tropism of herpes virus gene vectors. Both methods are based on the expression of glycoproteins having other properties in the helper cell during the packaging of viral gene vectors. The glycoproteins must have the property of being inserted into the capsid of these gene vectors which is ensured by specific protein domains of the glycoproteins. The expression of glycoproteins having a different cell tropism may on the one hand be achieved transiently by transfection of an expression plasmid which may be carried out simultaneously to the induction of the lytic cycle in the helper cells. On the other hand genes for glycoproteins having a different cell tropism may also be integrated into the helper virus genome or into the cellular chromosome to be available during the packaging of the gene vectors. Both methods lead to similar results. The functionally analogous gp350/220 glycoprotein of EBV on the helper virus genome may but may not necessarily be deleted.

Advantages Over the Prior Art

The method described permits the preparation of gene vectors packaged into a herpes virus capsid. The method is advantageous in that a helper cell line is used which does not release any helper viruses during the packaging of gene vectors. Up to now it was impossible to use this method with viruses having genomes larger than that of adenoviruses (36 kbp). It may be expected with certainty that this method may be extended to all large DNA viruses and helper cell lines derived therefrom (e.g. pox viruses, iridio viruses, baculoviruses and other herpes viruses). The preparation of such helper cell lines requires the cloning of these viral genomes into another organism, e.g. *E. coli,* to enable the targeted alteration of viral segments. The viral genomes prepared in this manner show the property of being able to produce all of the viral gene products for amplification and packaging of viral gene vectors while no helper virus is released. These gene vectors may also show novel properties so that they infect only cell type(s) which normally are not or only ineffectively infected by the helper virus. Selectivity of the cell tropism is an important prerequisite for the use of the gene vectors in gene therapy. It must be ensured that the vector-mediated transduction of genes of therapeutical interest occurs only into predetermined cells and not into any cell.

At this point, examples for further considered uses will be presented:

Herpes virus gene vectors carrying one or more genes instead of the gene of the 'green fluorescence protein' are of interest for use in gene therapy in humans. Therapeutical genes may be such which mediate novel properties to the recipient cells or the entire organism. These genes may serve to correct genetic diseases (e.g. ADA, thalassemia, lysosomal storage diseases, coagulation factor VIII etc.)

The expression of particular antigens may be used to employ the cells transduced by the gene vectors for immunization (e.g. as cellular anti-tumor vaccines against B and T cell lymphomas).

Gene vectors may bear one or more cytokins or other signal mediators having certain properties (such as anti-inflammatory cytokins) which may be used in a sensible manner locally in chronic arthritis and other diseases.

As already mentioned above an indispensable prerequisite for the practicability of the present invention is the possibility to provide a DNA helper virus vector DNA. In the following the preparation of a helper virus vector of this type containing a DNA virus genome ≧100 kbp will be described in more detail.

Up to now it has been impossible to alter or to delete any gene of DNA viruses ≧100 kbp, for example of EBV, with high efficiency. Thus, homologous recombination events between an EBV segment cloned in *E. coli* and the endogenous EBV present in cell lines infected in a latent manner are inaccurate, difficult to control and must be rendered detectable by means of co-transfected marker segments or selectable genes. In the present prior art, such approaches are not universally applicable, are slow and do not enable the alteration of genes or genomic segments of DNA viruses ≧100 kbp of EBV, such as those necessary for the maintenance of the EBV virus latent phase in the infected cells.

Thus, the disadvantages of the prior art are overcome by cloning the entire DNA virus genome of viruses having a size of ≧100 kbp in the form of a functional unit. A prerequisite of the cloning e.g. in *E. coli* as a recombinant molecule is the ability to integrate a so-called prokaryotic gene segment into the intact DNA virus genome. Integration of this segment containing functions for replication and a selectable marker for *E. coli* ensures that said recombinant molecule of a size of more than 100 kbp may be transfected e.g. into *E. coli* and stably replicated therein. In addition, this event ensures that a modification of any DNA virus segment e.g. in *E. coli* will be possible by means of conventional recombinant DNA technologies.

In the following the method of the invention will be explained with respect to a herpes virus, namely EBV, as an example.

The method described permits the preparation of recombinant herpes virus genomes which may be amplified as clones in *E. coli*. With complete certainty it will be possible to adopt this method for all large DNA viruses (such as pox viruses, iridio viruses, other herpes viruses, baculoviruses). Cloning of these viral genomes e.g. in *E. coli* will enable the simple modification by site-directed alteration of viral genes, the deletion thereof of the addition of other genes of interest. The resulting viral genomes will have novel properties depending on the genetic modification which enable for example the expression of foreign proteins in the corresponding target cells of the viruses.

The viral genomes cloned for example in *E. coli* present a product useful for the preparation of viral particles such as those suitable for encapsidation of recombinant plasmids or subgenomic viral segments.

The method is useful in the preparation of DNA virus vectors capable of replication in eukaryotic as well as prokaryotic cells and comprises at least the following steps of:

a) Introducing a DNA virus genome ≧100 kbp into an eukaryotic target cell and establishing such cells containing the viral DNA genome at least in extrachromosomal form;

b) introducing a DNA segment into the eukaryotic target cell at least comprising, operably linked to each other, the information for replication of the viral DNA genome in prokaryotic cells and at least one marker gene selectable in prokaryotic cells, and which is flanked by DNA segments (homologous segments) of the DNA virus genome having a length enabling recombination;

c) integrating the segments defined in (b) into the DNA virus genome by recombination; optionally d) selecting such target cells containing an extrachromosomal recombinant viral DNA genome; and optionally e) purifying and isolating the recombinant DNA virus vector genome.

This method differs from methods known to date for the preparation of DNA virus vectors particularly in that for the first time the preparation of such vectors from DNA viruses having a size of ≧100 kbp becomes possible. For example, in the method used up to now DNA viruses such as adenoviruses having a size of about 40 kbp were cloned. The preparation of DNA virus vectors having a size of ≧100 kbp, particularly ≧120 kbp, and preferably ≧150 kbp or especially preferred ≧170 kbp was impossible with the methods known from the prior art.

This method is not only useful for the preparation of recombinant herpes virus genomes reproducible in prokaryotic cells as well as in eukaryotic cells but also e.g. for the preparation of recombinant pox virus or iridio virus or baculovirus genomes.

The herpes virus may be an alpha herpes virus, a beta herpes virus, or a gamma herpes virus. Examples of those viruses are: alpha herpes virus: herpes simplex virus (HSV), varicella zoster virus (VZV); beta herpes virus: cytomegalovirus (CMV); gamma herpes virus: Epstein-Barr virus (EBV).

Introduction of the DNA virus into the eukaryotic target cell may be effected by methods known per se; examples of such methods are infection, transfection, or electroporation. The same applies to the introduction of the DNA segment into the eukaryotic target cell in step (b).

As an alternative to the process step (a) in which the DNA virus is introduced into the eukaryotic target cell such cells may be used which already contain the DNA virus in an extrachromosomal form.

A target cell according to the invention is meant to be any cell having virus receptors and in which the virus is able to replicate.

Furthermore, besides the DNA virus also a DNA segment is introduced into the eukaryotic target cell comprising at least the information for replication of the viral genome in prokaryotic cells and a marker gene which may be selected for in prokaryotic cells. These gene segments are flanked by DNA segments having a length which enables recombination with the DNA virus. The flanking DNA segments have homology to the DNA virus enabling a recombination, and particularly a homologous recombination. The length of the flanking DNA sequences preferably is $\geq 300$ bp, further preferred $\geq 1$ kbp and especially preferred $\geq 2$ kbp.

Preferably, integration of the segments described in step (b) into the DNA virus genome is carried out by homologous recombination in the DNA virus target cell. However, it is also possible that an illegitimate recombination will lead to the desired result. Normally, however, a homologous recombination will permit to achieve the recombining DNA virus genome.

The DNA segment in step (b) may be linearized prior to introduction into the eukaryotic target cell. In this manner, the ends will be protected against degradation by endogenous nucleases.

In a preferred embodiment of the invention the information for replication of the viral DNA genome will be localized in prokaryotes and the information for the marker gene selectable in prokaryotic cells will be on the *E. coli* F plasmid. In another preferred embodiment of the invention the DNA segment in step (b) will additionally contain at least one marker gene selectable in eukaryotic cells. As selectable markers any markers selectable in prokaryotic cells or in eukaryotic cells, respectively, may be used. Examples for such markers are in particular antibiotic resistance genes and fluorescence marker genes.

F factor-derived plasmids of about 5 kbp generally contain the following segments and genes of the *E. coli* F factor plasmid which in its naturally occuring form encompasses about 100 kbp: for maintaining the copy number of about 1 to 2 copies/*E. coli* cell the genes parA and parB are essential, oriS and the gene repE are necessary for DNA replication. All those elements are present on the F factor plasmid used for example for the generation of the EBV/F factor construct.

In a further embodiment the DNA segment in process step (b) contains at least one gene of interest encoding for example a protein of the blood coagulation cascade, e.g. the factor VIII gene. Any gene known per se may be localized on the DNA segment and may be introduced by the method of the invention into the DNA virus shuttle vector. In this manner it will be possible to express the gene of interest in an eukaryotic cell or in a prokaryotic cell.

This method enables the cloning of complete DNA virus genomes having a size of $\geq 100$ kbp. An especially preferred example is the EBV genome having a size of about 170 kbp.

In an embodiment the homologous regions in (b) are selected in a manner to introduce a mutation in the viral genome. A mutation according to the invention is meant to be a point mutation, a mutation affecting several nucleotides, a deletion, an addition, or an exchange of nucleotides. The addition of nucleotides also comprises the introduction of one or more genes encoding for example a gene of interest, mainly a gene of therapeutical value.

In an embodiment of the method the flanking regions in process step (b) are selected to delete the terminal repeats in the herpes virus genome. Following recombination with the DNA virus genome a packaging-deficient viral genome will be generated so that following induction of the lytic phase of EBV in the target cells no infectious particles will be released while simultaneously, however, all of the viral proteins and functions for the packaging of DNA molecules will be available in trans.

In another embodiment the recombinant DNA virus vector genome obtained will be mutated in further process steps. A definition of the understanding of 'mutation' according to the invention has been already given above. The introduction of mutations may be effected either in the way described above or by introducing the resulting DNA virus vector genome into a prokaryotic cell or into another eukaryotic cell and by introducing the mutations in those cells, for example by further recombination events. In a preferred embodiment of the invention a mutation is introduced in one or more of the cis-acting segments of the viral DNA genome where the mutation alters the packaging of the viral DNA genome.

In an embodiment of the invention which is particularly preferred according to the invention the prokaryotic portions of the DNA segment in step (b) will be selected to contain sequences with at least partial homology to each other having a length that enables homologous recombination whereby the prokaryotic portions of the DNA segment of (b) are eliminated. By such a homologous recombination the prokaryotic portions introduced by the method according to the invention are eliminated in subsequent process steps. In this manner, for example antibiotic resistances introduced by introduction of the DNA segment into the eukaryotic target cell and other prokaryotic portions may be removed yielding a DNA virus vector useful in gene therapy in which the proportion of prokaryotic foreign sequences is as low as possible. An example for this will be described in more detail in the Examples.

Furthermore, according to the invention a DNA virus vector is provided comprising at least a DNA virus genome $\geq 100$ kbp, at least a marker gene selectable in prokaryotic cells and the information for replication of the viral DNA genome in prokaryotic cells, operably linked to each other.

Into two different cell lines infected with two different EBV strains in a latent manner (B95.8 and P3HR1/HH514) a segment of the *E. coli* plasmid F factor was introduced comprising the functions for replication and a marker selectable in *E. coli*. This linear region of the F factor plasmid was flanked on the right and on the left each by EBV regions so that the F factor segment could be targeted into the endogenous EBV genome in the cell lines via two homologous recombination events. In addition to the flanking EBV regions the DNA fragment contains at least a marker gene suitable for selection (e.g. hygromycin phosphotransferase) or phenotypic characterization (e.g. green fluorescence protein, GFP) in eukaryotic cells. This construct is transfected into EBV-infected cells where homologous recombination with the endogenous EBV genome and the site-directed integration of the F factor segment together with the marker gene occur. Afterwards, the cell lines thus modified harbour a recombinant EBV genome which may be transferred into *E. coli* in a shuttle system. The recombinant EBV genome will replicate in *E. coli* via its F factor portion also carrying the prokaryotic selection marker. Other genetic alterations of the recombinant EBV genome may be effected using conventional genetic techniques in *E. coli*.

The recombinant EBV genome may be isolated from *E. coli* and the DNA molecules may be prepared using conventional techniques. These DNA molecules are then introduced by DNA transfer techniques stably or transiently into eukaryotic cells. The recombinant EBV genomes will replicate extrachromosomally in these cells such as in the cell lines B95.8 and P3HR1/HH514 infected in a latent manner. Spontaneously or following chemical induction.or induction effected by other means of the lytic phase of EBV the synthesis of recombinant Epstein-Barr virions will occur which are released into the cell culture supernatant and are available for other uses.

Methods of Preparation

Using the method described above, a F factor segment was introduced into the B95.8 virus genome containing the eukaryotic selection marker hygromycin phosphotransferase and the phenotypic marker gene GFP in addition to functional F factor components. The recombinant B95.8 genome was generated, transferred into *E. coli*, and recombinant EBV DNA was prepared from *E. coli*. This DNA was introduced into several EBV-negative cells (293, EBV-negative Akata, neuronal cells). Induction of the lytic cycle resulted in the release of infectious virions containing the recombinant EBV genome as the genetic information. These recombinant EBV genomes are able to e.g. immortalize primary human B lymphocytes.

In two independent experiments two different segments of the F factor were introduced into the P3HR1/HH514 virus genome into two different genomic sites. Targeting to these genomic sites was performed by different EBV flanking regions. In one experiment another EBV gene was introduced, in the second experiment a site-directed deletion of an EBV region was performed by selecting the EBV flanking regions.

The recombinant B95.8 as well as P3HR1/HH514 virus genomes were further modified in *E. coli* by deletions or introduction of new genes.

EXAMPLES

1. Cloning of a Fully Functional Genome of the B95.8 Strain

A F factor plasmid referred to as p1944.12 (Table 1) was generated in *E. coli* using conventional DNA cloning techniques. As shown schematically in FIG. 5 the plasmid contains two regions A and B representing the subgenomic regions of the B95.8 genome. The nucleotide sequence coordinates of these segments are reported in Table 1. The regions A and B flank the pMBO131 replicon (O'Connor et al., 1989) comprising the prokaryotic origin of replication of the F factor together with the selectable prokaryotic marker gene chloramphenicol acetyl transferase (cam). Furthermore, the eukaryotic marker gene hygromycin phosphotransferase (Hyg) expressed by the SV40 early promoter/enhancer and the marker gene green fluorescence protein (GFP) of the immediate early promoter/enhancer of human cytomegalovirus are contained in plasmid p1944.12 (Table 1 and FIG. 5). Portions of the p1944.12 plasmid important for function are the EBV segments, the pMBO131 portion and the Hyg, GFP genes are optional.

The regions A and B of the B95.8 genome on p1944.12 are selected to flank the natural deletion in the genome of B95.8 on the left and on the right. To introduce this plasmid into the B95.8 genome it was linearized with NotI restriction enzyme, and the free DNA ends were sealed by so-called hairpin oligonucleotides using T4 DNA ligase to protect them against exonucleases. The plasmid DNA thus modified was transfected into the B95.8 cells by electroporation and the cells were selected in the presence of 100 μg/ml of hygromycin. Under these selection conditions only cells survive which have taken up and integrated p1944.12 DNA either into the host cell genome or into the extrachromosomal genomic copies of the B95.8 EBV strain. To distinguish between those two possibilities single cell clones were investigated by Gardella agarose gels and subsequent Southern blot hybridization. By these analytical techniques it was possible to identify a number of cellular clones which had integrated p1944.12 into the genomic copies of the B95.8 EBV strain.

For the cloning of these genetically altered EBV genomes in *E. coli* the plasmid DNA was isolated from the cellular clones, transferred into *E. coli* strain DH10B using electroporation techniques and selected by means of chloramphenicol resistance. Subsequent isolation of plasmid DNA from *E. coli* resulted in DNA preparations which following digestion with several restriction enzymes showed DNA fragments corresponding exactly to the composition of B98.8 DNA including the integrated p1944.12 portion. The total size of these EBV genomes was more than 170 kbp and has been referred to as 2010.

2010 DNA was isolated in the microgram scale from *E. coli* and introduced into EBV-negative eukaryotic cells via several DNA transfection methods. These cells may be for example EBV negative Akata cells, 293 cells and fibroblast cells or cell lines. These cells were selected under adjusted hygromycin concentrations to ensure the stable introduction of 2010 DNA into the cells. The EBV lytic phase was induced by several techniques, such as by transfection of the BZLF1 expression plasmid pCMV-BZLF1 (Hammerschmidt and Sugden, 1988). Induction of the EBV lytic phase in these cells results in the release of infectious viruses capable of immortalizing primary human B lymphocytes. To detect this property of 2010 EBV a cell-free supernatant from lytically induced cells was obtained and used to infect primary human B lymphocytes. Four to six weeks after infection of these cells it was possible to establish permanently proliferating cell lines containing 2010 EBV DNA as was proven via different techniques (Southern blot hybridization, PCR analysis).

2. Cloning of a Packaging-deficient P3HR1/HH514 genome in *E. coli*

A F factor plasmid referred to as p2061.2 (Table 1) was generated in *E. coli* using conventional DNA cloning techniques. As shown schematically in FIG. 6 the plasmid contains two-regions A and B representing the subgenomic regions of the P3HR1/HH514 genome. The nucleotide sequence coordinates of these segments are reported in Table 1. The regions A and B flank the pMBO131 replicon (O'Connor et al., 1989) comprising the prokaryotic origin of replication of the F factor together with the selectable prokaryotic marker gene chloramphenicol acetyl transferase (cam). Furthermore, the eukaryotic marker gene hygromycin phosphotransferase (Hyg) expressed by the SV40 early promoter/enhancer is contained in plasmid p2061.2 (Table 1 and FIG. 6). Portions of the p2061.2 plasmid important for function are the EBV segments, the pMBO131/F factor portion and the Hyg gene.

The regions A and B of the P3HR1/HH514 genome on p2061.2 are selected to flank the 'terminal repeats' in the genome of P3HR1/HH514 on the left and on the right. The 'terminal repeats' (TR) are i.a. characterized by bearing signal sequences necessary for the packaging of viral genomic DNA into EBV capsids. The purpose of the construction of p2061.2 is to delete the TR signal sequences and to replace them by the pMB0131 and Hyg portions of p2061.2. To introduce p2061 into the P3HR1/HH514 genome it was linearized with SacI restriction enzyme, and the free DNA ends were sealed by so-called hairpin oligonucleotides using T4 DNA ligase to protect them against exonucleases. The plasmid DNA thus modified was transfected into the P3HR1/HH514 cells by electroporation and the cells were selected in the presence of 200 μg/ml of hygromycin. Under these selection conditions only cells survive which have taken up and integrated p2061.2 DNA either into the host cell genome or into the extrachromosomal genomic copies of the P3HR1/HH514 EBV strain. To distinguish between those two possibilities single cell clones were investigated by Gardella agarose gels and subsequent Southern blot hybridization. By these analytical techniques it was possible to identify a number of cellular clones which had integrated p2061.2 into the genomic copies of the P3HR1/HH514 EBV strain.

For the cloning of these genetically altered EBV genomes in *E. coli* the plasmid DNA was isolated from the cellular clones, transferred into *E. coli* strain DH10B using electroporation techniques and selected by means of chloramphenicol resistance. Subsequent isolation of plasmid DNA from *E. coli* resulted in DNA preparations which following digestion with several restriction enzymes showed DNA fragments corresponding exactly to the composition of P3HR1/HH514 genomic DNA without TR signal sequences but including the integrated p2061.2 portion. The total size of these EBV genomes was more than 170 kbp and has been referred to as 2087.2a.

2087.2a DNA was isolated in the microgram scale and introduced into EBV-negative eukaryotic cells via several DNA transfection methods. These cells may be for example EBV negative Akata cells, 293 cells and fibroblast cells or cell lines. These cells were selected under adjusted hygromycin concentrations to ensure the stable introduction of 2087.2a DNA into the cells. The EBV lytic phase was induced by several techniques, such as by transfection of the BZLF1 expression plasmid pCMV-BZLF1 (Hammerschmidt and Sugden, 1988). In contrast to the Example described in 1. the induction of the EBV lytic phase in these cells does not result in the release of infectious viruses since no packaging of EBV genomic DNA occurs due to the absence of TR packaging signals. However, these cell lines provide all viral functions for the packaging of DNA molecules in trans such as those necessary for the encapsidation of p554 (Hammerschmidt and Sugden, 1989) or of mini EBV plasmids (Kempkes et al., 1995a; Kempkes et al., 1995b) without releasing so-called helper virus (Hammerschmidt and Sugden, 1989).

3. Cloning of a P3HR1/HH514 Genome with Genetic Complementation in *E. coli*

A F factor plasmid referred to as p1820.15 (Table 1) was generated in *E. coli* using conventional DNA cloning techniques. As shown schematically in FIG. 7 the plasmid contains two regions A and B representing subgenomic regions of the B95.8 genome. The nucleotide sequence coordinates of these segments are reported in Table 1. The regions A and B flank the pMB0131 replicon (O'Connor et al., 1989) comprising the prokaryotic origin of replication of the F factor together with the selectable prokaryotic marker gene chloramphenicol acetyl transferase (cam). Furthermore, as functional regions the EBV gene EBNA2 and two exons of the EBV gene EBNA-LP are contained in the p1820.15 plasmid (Hammerschmidt and Sugden, 1989) (Table 1 and FIG. 7). Portions of the p1820.15 plasmid important for function are the flanking-EBV segments, the gene EBNA2 and the EBNA-LP gene portions as well as the pMBO131 portion.

The regions A and B of the B95.8 genome on p1820.15 are selected to flank the deletion which comprises two EBNA-LP exons and the entire EBNA2 gene in the genome of P3HR1/HH514 on the left and on the right. To introduce this plasmid into the P3HR1/HH514 genome it was linearized with NheI restriction enzyme, and the free DNA ends were sealed by so-called hairpin oligonucleotides using T4 DNA ligase to protect them against exonucleases. The plasmid DNA thus modified was transfected by electroporation into the P3HR1/HH514 cells together with the expression plasmid pCMV-BZLF1 which induces the EBV lytic cycle in these cells. Cell-free culture supernatant was obtained and used to infect primary human B lymphocytes. Four to six weeks following the infection of these cells permanently proliferating cell lines could be established. The deletion in P3HR1/HH514 comprising the entire EBNA2 gene and two exons of the EBNA-LP gene abolishes B cell immortalization. The regions on plasmid p1820.15 complement the deletion in the P3HR1/HH514 virus genome by homologous recombination between P3HR1/HH514 DNA and p1820.15 DNA similar to that described (Hammerschmidt and Sugden, 1989). The EBV genomes after homologous recombination are characterized by their restored ability to immortalize primary human B lymphocytes. At the same time the integration of the F factor portion of p1820.15 occurs making the pMB0131 replicon a component of the recombinant EBV genome.

For the cloning of these genetically altered EBV genomes in *E. coli* the plasmid DNA was isolated from the cellular clones, transferred into *E. coli* strain DH10B using electroporation techniques and selected by means of chloramphenicol resistance. Subsequent isolation of plasmid DNA from *E. coli* resulted in DNA preparations which following digestion with several restriction enzymes showed DNA fragments corresponding exactly to the composition of P3HR1/HH514 genomic DNA including the integrated p1820.15 portion. The total size of these EBV genomes was more than 170 kbp and has been referred to as 1947 (K clone).

4. Introduction of Mutations into Genomic EBV DNA Cloned into F Factor by Allelic Exchange The cloning of genomic EBV DNA in *E. coli* permits the simple genetic modification by means of methods which are established or adapted to, respectively, the specific conditions according to the invention.

To exchange the packaging signals in the cloned EBV genome 1947 (Table 1) the recombinant plasmid p2060.1 was generated in *E. coli* which consists of the following components (see FIG. 8):

1. A prokaryotic vector plasmid having a temperature-sensitive origin of replication (Tet shuttle plasmid) and the prokaryotic selection marker tetracycline resistance e.g. on the basis of pMBO96 (O'Connor et al., 1989).
2. Flanking regions A and B containing the EBV sequences of strain P3HR1/HH514 from nucleotide position #165,840 to #169,924 (A) and #1 to #3955 (B).
3. The eukaryotic selection marker hygromycin phosphotransferase expressed by the SV40 early promoter/enhancer. This gene is located between the EBV portions A and B and is indicated by 'mut' in FIG. 8.

The F factor plasmid 1947 (Table 1) is transfected into a recombination competent (recA+) *E. coli* strain, and the transfectants are identified by means of their chloramphenicol resistance. In a second step the Tet shuttle plasmid p2060.1 is transfected into the transfectants harbouring 1947 and the bacteria are selected at 30° C. for their double resistance against chloramphenicol and tetracycline. Both plasmids replicate independently of each other in the same E. coli cell. The homologous recombination via A (may also be effected via B) is forced by raising the temperature to 42° C. and selecting for resistance against chloramphicol and tetracycline, since the Tet shuttle plasmid p2060.2 is unable to replicate at this temperature. A co-integrate as shown in FIG. 8 is generated. By another homologous recombination, this time via B, the co-integrate is resolved and the Tet shuttle plasmid is lost so that the modification 'mut' (in this case hygromycin phosphotransferase) replaces the EBV sequence 'wt' (in this case the packaging signals TR). The last step takes place according to statistical distribution, i.e. during resolution of the co-integrate either the mutation 'mut' may be introduced (as shown in FIG. 8) or the starting situation 'wt' may be restored.

The advantage of this method in contrast to that described under 5. is the possibility to exchange even single nucleotides in the cloned EBV genome in a targeted manner without needing to introduce other foreign sequences.

5. Introduction of Mutations in Genomic EBV DNA Cloned into F Factor by Selective Integration A second alternative method for genetic modification of genomic EBV DNA cloned into F factor is the integration of linear DNA fragments by homologous recombination, as shown schematically in FIG. 9.

To mutate the EBV gene LMP2A, a Kan shuttle fragment was first cloned into a common pBR-derived plasmid, as shown in FIG. 9. The Kan shuttle fragment in plasmid p2120 contains two EBV segments A and B containing the EBV sequences of strain B95.8 from nucleotide positions #163, 473 to #166,180 (A) and #166,938 to #172,281/#1 to #649 (B). The mutation 'mut' indicated in FIG. 9 consists of two so-called loxP sequence motifs flanking an exon of the LMP2A EBV gene (EBV nucleotide positions #166,181 to #166,937). Contiguous with one of the two loxP sequence motifs there was cloned a selection marker for resistance against the antibiotic kanamycin bounded by FRT sequence motifs. The fragment as shown on the upper left in FIG. 9 is separated from the pBR portion by restriction enzymes and the linear Kan shuttle fragment DNA is isolated. Co-transfection of this linear DNA fragment together with the EBV genome 2010 cloned into F factor is performed into an E. coli strain which preferably is exonuclease V-negative; e.g. the E. coli strain BJ5183 (Hanahan, 1983). Selection of the transfected bacteria for resistance against chloramphenicol and kanamycin forces the homologous recombination between both of the DNA molecules and in the ideal case results in the EBV F factor plasmid shown on the upper right. The kanamycin resistance gene may be removed by site-directed recombination via FRT by FLP recombinase in E. coli. (Cherepanov and Wackernagel, 1995). As the result a mutated EBV F factor plasmid is generated. The basic difference as compared to the situation shown under 4. is the remaining of foreign sequences, namely of a FRT sequence motif.

Antibiotic resistance markers and sequences employed for site-directed recombination may be chosen as desired. This applies similarly also to the approach described in 4.

Moreover, the establishment of a genetic library is considered which may be prepared by transposon-mediated mutagenesis in E. coli and thus represents any large number of individually mutated EBV genomes. By random insertion of the transposon into the cloned EBV genomes a mutagenesis is generated at the site of insertion e.g. a disruption of the reading frame of the EBV gene. The advantage of an EBV genomic library of this type would be the possibility to biologically select for certain phenotypes. A genomic library containing mutated herpes virus genomes may be for example used as a screening system for antiviral substances.

Thus, the method may be further modified as follows:

(f) Introduction of a recombinant DNA virus vector genome into a prokaryotic cell;

(g) introduction of a plasmid into the prokaryotic cell containing at least a DNA sequence which bears a mutation compared to the homologous sequence present on the DNA virus vector genome, and a selectable marker gene flanked by DNA segments of a length sufficient to enable a recombination with the DNA virus vector genome, operably linked to each other;

(h) integration of the segment described in (g) by recombination into the DNA virus genome;

(i) optionally purification and isolation of the recombinant DNA vector.

In a further embodiment the plasmid in step (g) further contains sequence motifs which can be recognized by a recombinase; and prior to step (e) the resistance gene introduced by recombination is removed by site-directed recombination via the sequence motifs recognized by the recombinase.

Removal of the prokaryotic replicon and of other foreign portions from the herpes virus genome cloned in E. coli.

Using the gene vectors it is desirable to keep the portion of genetic information introduced into the target cell as small as possible and to restrict it to essential features. In particular, subgenomic segments are undesirable which harbour prokaryotic marker genes such as antibiotic resistances or otherwise represent a potential safety hazard because they may be the reason for homologous recombinations with several bacteria. The EBV genomes cloned using the F factor replicon are such a hybrid molecule. The F factor portion is essential for the propagation of the DNA molecule in E. coli but is completely non-functional in the eukaryotic cell into which the EBV/F factor replicon modified in E. coli is then introduced to prepare genetically modified EBV.

Surprisingly, a convenient method for the complete removal of this F factor portion without further genetic manipulation has been discovered.

In the cloning of a fully functional genome of strain B95.8 in E. coli a F factor plasmid has been used named p1944.12 (Table 1). This was prepared in E. coli using conventional DNA cloning techniques. As shown schematically in FIG. 5, the plasmid consists of two segments A and B representing subgenomic regions of the B95.8 genome. The nucleotide sequence coordinates of these regions are presented in the Table 1; they extend from EBV coordinate #143,458 to #152,636 in region A and from #149,930 to #159,880 in region B. The regions A and B flank the pMBO131 replicon (O'Connor et al., 1989) comprising the prokaryotic origin of replication of the F factor together with the selectable prokaryotic marker gene chloramphenicol acetyl transferase (cam) and other genes. Both of the EBV portions are selected to contain in part the same DNA sequence regions, in the actual example a partial duplication of 2.7 kbp (from #149,930 to #152,636). The F factor plasmid cloned from these experiments in E. coli was named 2010 (Table 1). Following transfection of the 2010 DNA into 293 cells homologous recombination events occur spontaneously between the duplicated portions in the regions A and B in these cells leading to the deletion of all sequences derived from the prokaryotic cloning steps. At this point, examples for further considered uses will be presented:

Establishment of specifically modified DNA viruses lacking particular virulent genes which may be used as specifically attenuated vaccine strains. In the case of EBV possible virulent genes may be for example EBNA2, LMP1, LMP2A and so on which may be deleted for the purpose of attenuation of the vaccine strain.

Generation of recombinant EBV vectors which in packaging cell lines are provided with an EBV capsid and may be used in gene transfer into human cells or cells of other mammals in vitro or in vivo. These packaging cell lines stably contain an EBV genome or the essential parts thereof necessary for the production of viral structural proteins to package the EBV vectors. The packaging cell lines are preferably provided with an EBV genome lacking its own packaging signals (see FIG. 6 and embodiments) to prevent the release of undesired so-called helper viruses. The EBV vectors which may be packaged may be based on conventional recombinant DNA plasmids containing all of the elements necessary for amplification of their DNA (oriLyt), their packaging (TR), and the stable extrachromosomal existence in the recipient cell (oriP and EBNA1). In addition, these vectors may bear genes of therapeutical interest e.g. factor VIII, in the sense of a genetic correction.

Moreover the affinity of such vectors for certain target cells may be altered. EBV glycoproteins responsible for the infection of specific cells (normally B cells and some epithelial cells) may be altered by mutation of the EBV genomes cloned into F factor in *E. coli* or replaced by others. An example for an extended cell tropism may be the vesicular stomatits virus glycoprotein G, an example for an extremely specific cell tropism for almost exclusively pluripotent hematopoietic stem cells would be the ligand for stem cell factor receptor on the stem cell, the membrane-bound stem cell factor ligand (mSCF ligand). This so-called pseudo-typing is particularly attractive for herpes virus vectors since the glycoproteins important for infectiousness are embedded into a phospholipid membrane derived from a nuclear membrane. This membrane is essentially unstructured and only loosely encapsulates the strictly geometrical capsid of the virion. In contrast to many smaller viruses (e.g. adenovirus, adeno-associated virus (AAV), retroviruses) the capsid of herpes viruses and other large DNA viruses is flexible and requires no specific protein configuration or folded structures which otherwise would prevent virus maturation and assembly.

Advantages Over the Prior Art

The method described permits for example the preparation of recombinant herpes virus genomes which may be clonally amplified for example in *E. coli*. It may be expected with certainty that this method may be applied to all large DNA viruses (e.g. pox viruses, iridio viruses, other herpes viruses). Cloning of these viral genomes e.g. in *E. coli* allows the simple modification by targeted alterations of viral genes, their deletion or the addition of further genes of interest. The viral genomes prepared in this manner show novel properties depending on the genetic modification such as permitting the expression of proteins in the respective target cells of the viruses.

The viral genomes cloned in *E. coli* provide a product useful for example for encapsidation of recombinant plasmids or subgenomic viral regions.

REFERENCES

Baer, R., Bankier, A. T., Biggin, M. D., Deininger, P. L., Farrell, P. J., Gibson, T. J., Hatfull, G., Hudson, G. S., Satchwell, S. C., Seguin, C., Tufnell, P. S., und Barell, B. G. (1984). DNA sequence and expression of the B95-8 Epstein-Barr virus genome. Nature (London) 310, 207–211.

Cohen, J. I., Wang, F., Mannick, J., und Kieff, E. (1989). Epstein-Barr virus nuclear protein 2 is a key determinant of lymphocyte transformation. Proc. Natl. Acad. Sci. U S A 86, 9558–9562.

Hammerschmidt, W., und Sugden, B. (1988). Identification and characterization of oriLyt, a lytic origin of DNA replication of Epstein-Barr virus. Cell 55, 427–433.

Hammerschmidt, W., und Sugden, B. (1989). Genetic analysis of immortalizing functions of Epstein-Barr virus in human B lymphocytes. Nature (London) 340, 393–397.

Hammerschmidt, W., und Sugden, B. (1995a). Immortalized lymphocytes for production of viral-free proteins (USA, Canada, Mexico, Japan.

Kempkes, B., Pich, D., Zeidler, R., und Hammerschmidt, W. (1995a). Immortalization of human primary B-lymphocytes in vitro with DNA. Proc. Natl. Acad. Sci. USA 92, 5875–5879.

Kempkes, B., Pich, D., Zeidler, R., Sugden, B., und Hammerschmidt, W. (1995b). Immortalization of human B-lymphocytes by a plasmid containing 71 kpb of Epstein-Barr viral DNA. J. Virol. 69, 231–238.

Moore, M. D., Cooper, N. R., Tack, B. F., und Nemerow, G. R. (1987). Molecular cloning of the cDNA encoding the Epstein-Barr virus/C3d receptor (complement receptor type 2) of human B lymphocytes Proc. Natl. Acad. Sci. USA 84, 9194–9198.

Nemerow, G. R., Houghten, R. A., Moore, M. D., und Cooper, N. R. (1989). Identification of an epitope in the major envelope protein of Epstein-Barr virus that mediates viral binding to the B lymphocyte EBV receptor (CR2). Cell 56, 369–377.

Yates, J. L., Warren, N., und Sugden, B. (1985). Stable replication of plasmids derived from Epstein-Barr virus in various mammalian cells. Nature (London) 313, 812–815.

Zimmermann, J., und Hammerschmidt, W. (1995). Structure and role of the terminal repeats of Epstein-Barr virus in processing and packaging of virion DNA. J. Virol. 69, 3147–3155.

Cherepanov, P. P. und Wackernagel, W. (1995). Gene disruption in *Escherichia coli*: TcR and KmR cassettes with the option of Flp-catalyzed excision of the antibiotic-resistance determinant. Gene, 158, 9–14.

Hammerschmidt, W. und Sugden, W. M. (1993) U.S. Pat. No. 5,194,601.

Hammerschmidt, W. und Sugden, B. (1995) EP-A-0 694 613.

Hanahan, D. (1983). Studies on transformation of *Escherichia coli* with plasmids. J. Mol. Biol., 166, 557–580.

O'Connor, M., Peifer, M. und Bender, W. 11989). Construction of large DNA segments in *Escherichia coli*. Science, 244, 1307–1312.

Firth, N., Ippen-Ihler, K., und Skurray, R. A. (1996). Structure and function of the F factor and mechanism of conjugation. In *Escherichia coli* and Salmonella, F. C. Neidhardt, R. Curtiss III, J. L. Ingraham, E. C. C. Iin, K. B. Low, B. Magasnik, W. S. Reznikoff, M. Riley, M. Schaechter und H. E. Umbarger, eds (Washington, D.C.: American Society for Microbiology Press, 2377–2401).

Shizuya, H., Birren, B., U. J., Mancino, V., Slepak, T., Tachiiri, Y., und Simon, M. (1992). Cloning and stable maintenance of 300-kilobase-pair fragments of human DNA in *Escherichia coli* using an F-factor-based vector. Proc. Natl. Acad. Sci. USA 89, 8794–8797.

TABLE 1

| EBV genome | F factor plasmid | EBV locus | EBV left coordinates | pMBO131 replicon | hygromycin phospho-transferase | EBNA2/ EBNA-LP | Green fluorescence protein | EBV right coordinates |
|---|---|---|---|---|---|---|---|---|
| 2010 | p1944.12 | deletion in B95.8 | #143,458-#52,636 (BsaBI/BsaBI) | yes | yes | no | yes | #149,930-#159,880 (ClaI/AscI) |
| 2087.2a | p2061.2 | terminal repeats (TR) in P3HR1/HH514 | #165,840-#169,924 (BstEII/BstEII) | yes | yes | no | no | #1-#3959 (EcoRI/BamHI) |
| 1947 (K clone) | p1820.15 | EBNA2 deletion in P3HR1/HH514 | #8994-#50,304 (EcoRI/PmeI) | yes | no | yes | no | #50,305-#56,083 (PmeI/SalI) |

Legend: EBV locus indicates the genomic location into which the linearized F factor plasmids p1820.15, p1944.12 or p2061.2 were introduced by homologous recombination. As the EBV strains were used either the prototype strain B95.8 or the P3HR1/HH514 strain. The EBV regions flanking the linearized plasmids as homologous EBV genomic fragments are indicated by their EBV coordinates which refer to the prototype strain B95.8 and which are present in comparable form also in P3HR1/HH514. pMBO131 indicates the portion of the *E. coli* F factor plasmid. Hygromycin phosphotransferase and EBNA2/EBNA-LP refer to genes permitting the selection for homologous recombination events between the EBV strains (B95.8 or P3HR1/HH514) and the linearized F factor plasmids p1820.15, p1944.12 or p2061.2. Green fluorescence protein is a phenotypic marker gene.

What is claimed is:

1. Method for helper virus-free packaging of a gene vector DNA into the viral particles of a DNA herpes virus comprising the steps of:
   a) introducing a DNA helper herpes virus vector DNA on one or two DNA molecules comprising:
      (α) a total size of ≧100 kbp of said DNA helper herpes vector DNA;
      (β) at least one mutation which renders one or more of the cis-acting signal sequences for packaging of the DNA helper virus vector DNA non-functional;
      (γ) a sequence for production of DNA virus particles of the DNA helper virus which do not contain a helper virus genome;
      (δ) a sequence for a marker gene selectable in eukaryotic cells; into an eukaryotic cell;
   b) establishing of a cell line containing the DNA herpes helper virus vector DNA in a stable manner;
   c) introducing a gene vector DNA to be packaged comprising;
      (α) a cis-acting signal sequence for packaging of the gene vector DNA into a viral particle of the DNA helper virus;
      (β) a gene of interest; into the eukaryotic cell;
   d) inducing a lytic phase of the DNA helper virus and producing proteins important for packaging of the DNA helper virus;
   e) packaging of the gene vector DNA into the viral particles of the DNA helper virus; optionally
   f) releasing the viral particles containing the gene vector DNA; and/or (g) optionally purifying the viral particles.

2. Method according to claim 1, wherein said herpes helper virus DNA comprises a genome size of ≧120 kbp.

3. Method according to claim 1, wherein said DNA helper virus vector DNA comprises a sequence controlling replication of the viral DNA genome in prokaryotic cells and optionally at least one marker gene selectable in prokaryotic cells.

4. Method according to claim 1, wherein said DNA helper virus vector DNA comprises at least portions of the EBV DNA.

5. Method according to claim 1, wherein said cis-acting signal sequences comprise the terminal repeat sequences of EBV, or the lytic origin of replication of EBV.

6. Method according to claim 1, wherein said eukaryotic cell is a human cell.

7. Method according to claim 1, wherein said gene of interest is a gene of therapeutical value.

8. Method according to claim 1, further comprising introducing into the eukaryotic cell a gene for effecting a cell tropism of the DNA helper virus.

9. Method according to claim 8, wherein the gene affecting the cell tropism is present on the gene vector DNA.

10. Method according to claim 2, wherein said genome size is ≧150 kbp.

11. Method according to claim 10, wherein said genome size is ≧170 kbp.

12. Eukaryotic helper cell for helper virus-free packaging of gene vector DNA into the virus particles of a DNA helper herpes virus comprising:
   (a) a DNA helper herpes virus vector DNA ≧100 kbp on one or two molecule(s) carrying a mutation which renders one or more of the cis-acting signal sequences for packaging non-functional and including a sequence controlling production of the DNA virus particles which do not contain a helper virus genome and a sequence for a marker gene selectable in eukaryotic cells;
   (b) a gene vector DNA comprising at least
      (α) a cis-acting signal sequence for packaging of the gene vector DNA into a viral particle of the DNA helper virus;
      (β) a gene of interest.

13. Eukaryotic helper cell according to claim 12, comprising at least portions of EBV as the helper virus vector DNA.

14. Eukaryotic helper cell according to claim 12, wherein said cell is a human cell.

15. Eukaryotic helper cell according to claim 13, wherein the herpes virus vector DNA is EBV DNA.

* * * * *